(12) United States Patent
Muldoon et al.

(10) Patent No.: US 11,511,281 B2
(45) Date of Patent: Nov. 29, 2022

(54) FLUID TRANSFER DEVICE, SYSTEM AND METHOD

(71) Applicant: EMD Millipore Corporation, Burlington, MA (US)

(72) Inventors: Joseph Muldoon, Berlin, MA (US); Rene Reinbigler, Kirchheim (FR)

(73) Assignee: EMD Millipore Corporation, Burlington, MA (US)

( * ) Notice: Subject to any disclaimer, the term of this patent is extended or adjusted under 35 U.S.C. 154(b) by 297 days.

(21) Appl. No.: 16/878,522

(22) Filed: May 19, 2020

(65) Prior Publication Data

US 2020/0276587 A1    Sep. 3, 2020

Related U.S. Application Data

(62) Division of application No. 15/518,298, filed as application No. PCT/US2015/055538 on Oct. 14, 2015, now Pat. No. 10,688,495.

(Continued)

(51) Int. Cl.
*B01L 3/00* (2006.01)
*A61B 5/15* (2006.01)
(Continued)

(52) U.S. Cl.
CPC ............ *B01L 3/56* (2013.01); *A61B 5/15003* (2013.01); *A61B 5/150221* (2013.01);
(Continued)

(58) Field of Classification Search
None
See application file for complete search history.

(56) References Cited

U.S. PATENT DOCUMENTS 3,865,411 A   2/1975   Rowe et al.
4,022,205 A   5/1977   Tenczar
(Continued)

FOREIGN PATENT DOCUMENTS

CA    2519367 A1    9/2004
JP    H08502339 A   3/1996
(Continued)

OTHER PUBLICATIONS

International Search Report and Written Opinion received for PCT Application No. PCT/US2015/055538, dated Apr. 6, 2016, 14 pages.

(Continued)

*Primary Examiner* — Matthew D Krcha
*Assistant Examiner* — Brittany I Fisher
(74) *Attorney, Agent, or Firm* — EMD Millipore Corporation

(57) ABSTRACT

A fluid transfer device includes a syringe barrel having a chamber, a first plunger slidably movable inside the chamber, and a second plunger slidably movable inside the chamber. The distal end portion of the first plunger is engageable with the proximal end portion of the second plunger such that when the distal end portion of the first plunger and the proximal end portion of the second plunger are engaged, the second plunger is movable by the first plunger. A check valve may be incorporated into the distal end portion of the second plunger to allow a fluid to pass therethrough in a direction towards the proximal end portion of the second plunger and prevent a fluid to pass therethrough in a reverse direction. A fluid transfer assembly and a sampling method are also described.

8 Claims, 11 Drawing Sheets

Related U.S. Application Data

(60) Provisional application No. 62/110,264, filed on Jan. 30, 2015.

(51) Int. Cl.

| | | |
|---|---|---|
| *G01N 1/14* | (2006.01) | |
| *A61M 5/178* | (2006.01) | |
| *A61M 5/31* | (2006.01) | |
| *A61M 5/315* | (2006.01) | |
| *A61B 5/153* | (2006.01) | |

(52) U.S. Cl.
CPC .. *A61B 5/150236* (2013.01); *A61B 5/150244* (2013.01); *A61B 5/150251* (2013.01); *A61B 5/150992* (2013.01); *B01L 3/502* (2013.01); *G01N 1/14* (2013.01); *A61B 5/153* (2013.01); *B01L 2200/141* (2013.01); *B01L 2300/0832* (2013.01); *B01L 2300/0864* (2013.01); *B01L 2400/0475* (2013.01); *B01L 2400/0478* (2013.01); *B01L 2400/0611* (2013.01)

(56) References Cited

U.S. PATENT DOCUMENTS

| | | | |
|---|---|---|---|
| 4,030,494 | A | 6/1977 | Tenczar |
| 4,418,945 | A | 12/1983 | Kellogg |
| 5,393,101 | A | 2/1995 | Matkovich |
| 5,522,804 | A | 6/1996 | Lynn |
| 6,296,764 | B1 | 10/2001 | Guirguis et al. |
| 7,918,243 | B2 | 4/2011 | Diodati et al. |
| 8,544,497 | B2 | 10/2013 | Hillier et al. |
| 2003/0030272 | A1 | 2/2003 | Johnson et al. |
| 2005/0054238 | A1 | 3/2005 | Matkovich et al. |
| 2007/0269355 | A1 | 11/2007 | Malmqvist |
| 2010/0230950 | A1 | 9/2010 | Williams et al. |
| 2011/0046602 | A1* | 2/2011 | Grimm ................ A61M 5/284 141/2 |
| 2012/0136298 | A1* | 5/2012 | Bendix ............ A61M 5/31515 29/428 |
| 2013/0048111 | A1 | 2/2013 | Gebauer |
| 2013/0048670 | A1 | 2/2013 | Greter |
| 2013/0289517 | A1 | 10/2013 | Williams et al. |
| 2015/0028586 | A1 | 1/2015 | Gerst et al. |

FOREIGN PATENT DOCUMENTS

| | | |
|---|---|---|
| JP | 2002-510996 A | 4/2002 |
| JP | 2002-514941 A | 5/2002 |
| WO | 1995/21639 A1 | 8/1995 |
| WO | 96/30076 A1 | 10/1996 |
| WO | 1998/46136 A1 | 10/1998 |
| WO | 98/50105 A1 | 11/1998 |
| WO | 2008/137578 A1 | 11/2008 |

OTHER PUBLICATIONS

Office Action received for Canadian Patent Application No. 3,080,140 dated Jun. 10, 2022, 3 Pages.

* cited by examiner

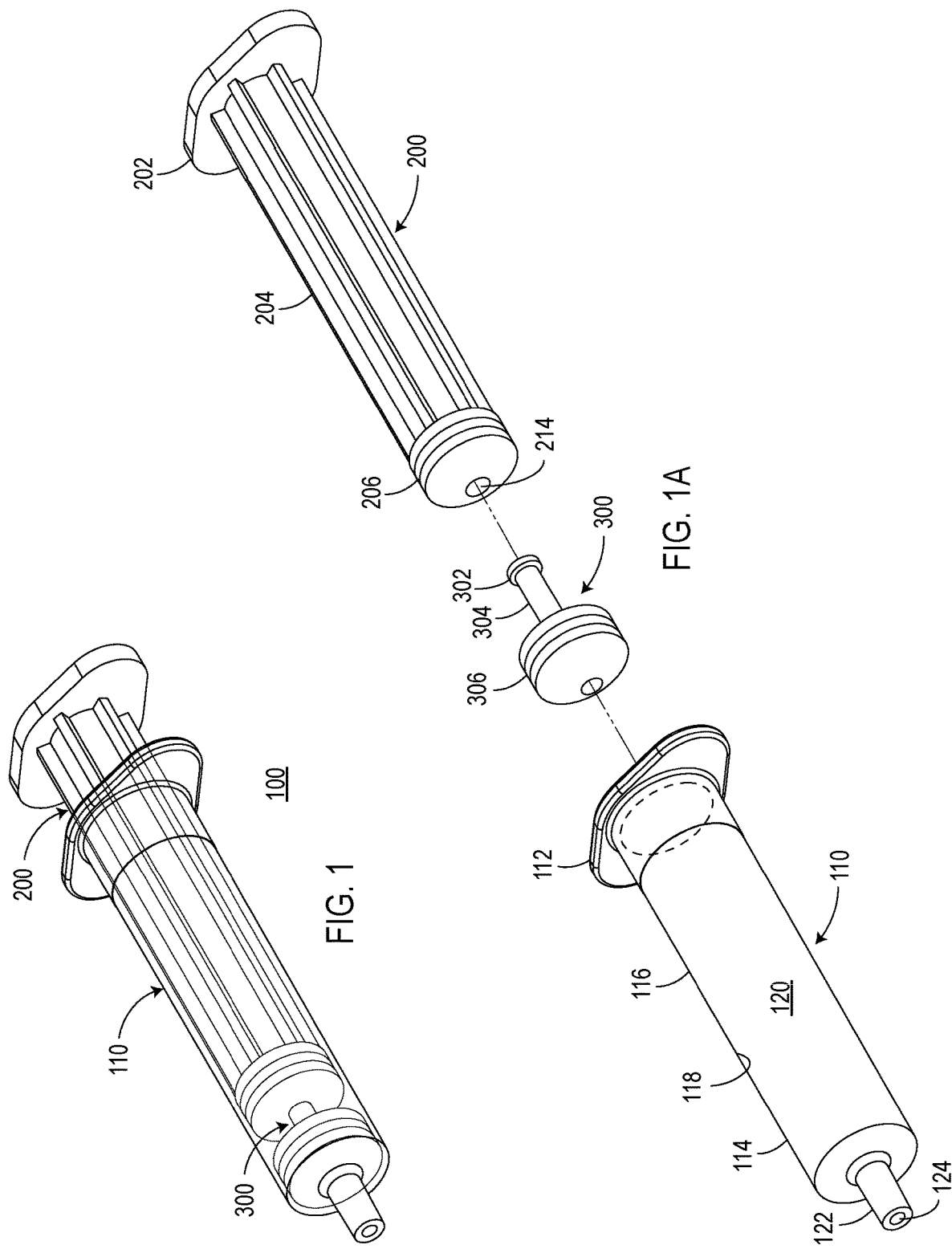

FLUID TRANSFER DEVICE, SYSTEM AND METHOD

RELATED APPLICATIONS

This application is a continuation of U.S. application Ser. No. 15/518,298, filed on Apr. 11, 2017, which is a US National Stage application of International Application No. PCT/US2015/055538, filed Oct. 14, 2015, which claims priority of U.S. Provisional Application Ser. No. 62/110,264 filed on Jan. 30, 2015, the disclosure of which is incorporated herein by reference in its entirety.

TECHNICAL FIELD

Embodiments of this disclosure relate generally to fluid transfer devices, systems and methods. In particular, various embodiments of fluid sampling devices and methods are described.

BACKGROUND

In pharmaceutical, biotechnology, food, beverage, and other industries, it is often desired to take many samples to monitor process development and/or optimize process steps. Conventional fluid sampling is commonly conducted with a needle-free sampling valve connected to a reactor or other processing vessels via small diameter tubing. The operator first swabs the connection of the sampling valve with a cleaner, typically an ethanol or methanol solution. Next a standard syringe is connected and a full sample is drawn, disconnected, and discarded. This is done to clear the tubing and valve of any dead leg which would result in an inaccurate reading. Then, the sampling valve is cleaned again and a new syringe is connected to take a representative sample.

The conventional process of cleaning is operator-dependant and can easily be missed or improperly conducted. Further, to get a sample, the operator needs to connect twice to the system with different sampling devices, doubling the chance of contamination. Therefore, there is a need for an improved fluid transfer device, system, and method that can overcome the various disadvantages in conventional fluid sampling.

SUMMARY

Certain embodiments of a fluid transfer device, assembly, and method are set forth below. It should be understood that these embodiments are presented merely to provide the reader with a brief summary of certain forms the invention might take and that these embodiments are not intended to limit the scope of the invention. Indeed, the invention may encompass a variety of embodiments or aspects that may not be set forth below.

In one aspect, a fluid transfer device includes a syringe barrel having a chamber, a first plunger slidably movable inside the chamber, and a second plunger slidably movable inside the chamber. The distal end portion of the first plunger is engageable with the proximal end portion of the second plunger such that when the distal end portion of the first plunger and the proximal end portion of the second plunger are engaged, the second plunger is movable by the first plunger. When the distal end portion of the first plunger and the proximal end portion of the second plunger are not engaged, the first plunger is movable relative to the second plunger. A check valve may be incorporated into the distal end portion of the second plunger to allow a fluid to pass therethrough in a direction to the proximal end portion of the second plunger and prevent a fluid to pass therethrough in a direction from the proximal end portion of the second plunger.

In another aspect, a fluid transfer assembly includes a first fluid transfer device that can couple to a fluid source and a second fluid transfer device that can couple to the first fluid transfer device. The first fluid transfer device comprises an interface structure and the second fluid transfer device comprises an interface structure complementary to the interface structure of the first fluid transfer device to allow the second fluid transfer device to slidably move in positioning with the first fluid transfer device. The interface structure of the first fluid transfer device may comprise one or more tongues, and the interface structure of the second fluid transfer device may comprise one or more grooves complementary to the one or more tongues, thereby allowing the second fluid transfer device to slidably move in positioning with the first fluid transfer device. Alternatively, The interface structure of the first fluid transfer device may comprise one or more grooves and the interface structure of the second fluid transfer device may comprise one or more tongues complementary to the one or more grooves.

In a further aspect, a method of sampling a fluid source comprises connecting a fluid source with a fluid transfer assembly which comprises a first fluid transfer device coupled to the fluid source and a second fluid transfer device coupled to the first fluid transfer device, and drawing a sample from the fluid source into the second fluid transfer device via the first fluid transfer device. The first fluid transfer device comprises an interface structure and the second fluid transfer device comprises an interface structure complementary to the interface structure of the first fluid transfer device. In connecting the fluid transfer assembly with the fluid source, the second fluid transfer device is slidably move to position with the first fluid transfer device via the interface structures of the first and second fluid transfer devices. In some embodiments, the method further comprises replacing the second fluid transfer device with a third fluid transfer device. Replacing the second fluid transfer device comprises slidably displacing the second fluid transfer device from the first fluid transfer device and slidably positioning the third fluid transfer device with the first fluid transfer device.

BRIEF DESCRIPTION OF THE DRAWINGS

These and various other features and advantages will become better understood upon reading of the following detailed description in conjunction with the accompanying drawings and the appended claims provided below, where:

FIG. 1 is a perspective view of a fluid transfer device according to some embodiments of the disclosure;

FIG. 1A is an exploded view of the fluid transfer device of FIG. 1, showing a syringe barrel, a first plunger, and a second plunger respectively;

DETAILED DESCRIPTION

Figure 1B:
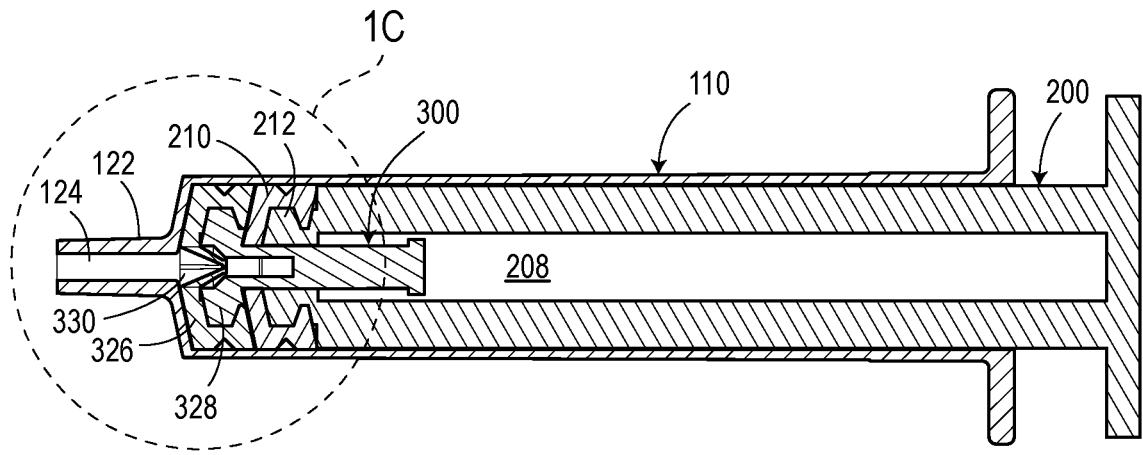
FIG. 1B is a cross-sectional view of a fluid transfer device according to some embodiments of the disclosure.

Various embodiments of a fluid transfer device, system, and method are described. It is to be understood that the disclosure is not limited to the particular embodiments described as such may, of course, vary. An aspect described in conjunction with a particular embodiment is not necessarily limited to that embodiment and can be practiced in any other embodiments.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. In the following description, well known components or steps may not be described in detail in order to avoid unnecessarily obscuring the embodiments of the disclosure.

As used herein, the phrase "proximal end portion" refers to a portion, including an extreme end, of a device, member or component that is closer to a user when in use. The phrase "distal end portion" refers to a portion, including an extreme end, of a device, member or component that is farther to a user when in use.

Exemplary embodiments of a fluid transfer device, system, and method will now be described with reference to the figures. It should be noted that some figures are not necessarily drawn to scale. The figures are only intended to facilitate the description of specific embodiments, and are not intended as an exhaustive description or as a limitation on the scope of the disclosure.

Referring to FIGS. 1 to 6, various embodiments of a fluid transfer device 100 according to one aspect of the disclosure will now be described.

As shown FIGS. 1 and 1A, the fluid transfer device 100 includes a syringe barrel 110, a first plunger 200, and a second plunger 300. The first plunger 200 is slidably movable inside the syringe barrel 110 and includes a proximal end portion 202, an elongate body portion 204, and a distal end portion 206. The second plunger 300 is also slidably movable inside the syringe barrel 110 and includes a proximal end portion 302, an elongate body portion 304, and a distal end portion 306. The distal end portion 206 of the first plunger 200 is engageable with the proximal end portion 302 of the second plunger 300 such that when the distal end portion 206 of the first plunger 200 and the proximal end portion 302 of the second plunger 300 are engaged, the second plunger 300 is movable by the first plunger 200, and when the distal end portion 206 of the first plunger 200 and the proximal end portion 302 of the second plunger 300 are disengaged, the first plunger 200 is movable relative to the second plunger 300.

Referring to FIG. 1A, the syringe barrel 110 may include a proximal end portion 112, a distal end portion 114, and an elongate body portion 116. The proximal end portion 112 may be open ended and may have a finger grip, flange, or the like for holding the device, for example, when the first plunger 200 is being moved relative to the syringe barrel 110. The elongate body portion 116 has an inside surface 118 defining a chamber 120 for retaining fluid. The elongate body portion 116 may generally be in a cylindrical shape or any other suitable shapes. The distal end portion 114 may include a tip 122 having a passageway 124 in fluid communication with the chamber 120. The tip 122 may be configured to be inserted into a sampling device. For example, the tip 122 may be configured to engage with a luer sampling valve, which in turn may be connected to a fluid source via suitable tubing. Alternatively, the tip 122 may be configured to be inserted to a fluid source directly. The fluid source may include a reactor or vessel in which a process such as a pharmaceutical, biopharmaceutical, food, or beverage process or the like is conducted, or any conduit connected to the reactor or vessel. The syringe barrel 110 may be constructed from any suitable material such as plastic, glass, metal or the like.

Referring to FIGS. 1A and 1B, the first plunger 200 is slidably movable inside the syringe barrel 110 and includes a proximal end portion 202, an elongate body portion 204, and a distal end portion 206. The elongate body portion 204 may have a cross-section with an outer dimension smaller than the internal diameter of the syringe barrel 110 to allow the first plunger 100 to slidably move relative to the syringe barrel 110. The elongate body portion 204 of the first plunge 200 may be hollow or have an internal channel 208 extending from the proximal end portion 202 to the distal end portion 206 through some or all of the elongate body portion 204, and may further extend to the proximal end portion of 202 (FIG. 1B). The exterior of the elongate body 204 may generally be cylindrical or in any other suitable shape to facilitate the movement of the first plunger 200 inside the syringe barrel 110.

The proximal end portion 202 of the first plunger 200 may have a finger grip, flange or the like for holding and moving the first plunger 200 relative to the syringe barrel 110. The distal end portion 206 of the first plunger 200 provides a liquid tight seal around the circumference of the distal end 206 against the inside surface 118 of the syringe barrel 110. The distal end portion 206 or part of the distal end portion 206 of the first plunger 200 may be constructed with a suitable sealing material, e.g. an elastomeric polymer, to provide a circumferential seal between the distal end portion 206 and the inside surface 118 of the syringe barrel 110. Alternatively, the circumferential seal may be provided by one or more separate seal members coupled to the distal end portion of the first plunger 200. An exemplary seal member 210 shown in FIGS. 1B and 1C may generally be in the shape of a cup having an annular side and a base defining an interior or receptacle configured to receive the distal end portion 212 of the elongate body portion 204 of the first plunger 200. The exterior surface of the annular side of seal member 210 may have annular rims and a recess therebetween to provide a stable fluid-tight seal against the inside surface 118 of the syringe barrel 110. The interior surface of the annular side and the base of the seal member 210 may be configured such that the receptacle defined by the interior surface conforms to the shape of the distal end portion 212 of the elongate body portion 204 of the first plunger 200. By way of example, the distal end 212 may have a reduced cross-sectional dimension and a groove between the distal end portion 212 and the elongate body portion 204. The seal member 210 may include an annular edge having an inwardly extended flange to be received in the groove. Therefore, in some embodiments, the distal end portion 206 of the first plunger 200 may include a combination of the seal member 210 and the distal end 212 of the elongate body portion 204. The seal member 210 and the distal end portion 212 may have a pass-through or an opening 214 (FIG. 1A) configured to allow the elongate body portion 304 of the second plunger 300 to extend therethrough into the internal channel 208 of the elongate body portion 204 of the first plunger 200, as will be described in greater detail below.

Still referring to FIGS. 1A and 1B, the second plunger 300 is slidably movable inside the syringe barrel 110 and includes a proximal end portion 302, an elongate body portion 304, and a distal end portion 306. The distal end portion 306 of the second plunger 300 provides a liquid tight seal along the circumference of the distal end against the inside surface 118 of the syringe barrel 110. The circumferential seal may be provided by one or more separate seal members coupled to the distal end portion of the second plunger 300. An exemplary seal member 326 shown in FIGS. 1B and 1C may have a shape similar to the seal member 210 coupled to the distal end portion 212 of the first plunger 200. For example, the seal member 326 coupled to the distal end portion 328 of the elongate body portion 304 of the second plunger 300 may generally be in the shape of a cup having a base and an annular side defining an interior or receptacle configured to receive the distal end portion 328 of the second plunger 300. The exterior surface of the annular side of the seal member 326 may have annular rims and a recess therebetween to provide a stable fluid-tight seal against the inside surface 118 of the syringe barrel 110. The interior surface of the annular side and base of the seal member 326 may be configured such that the receptacle defined by the interior surface conforms to the shape of the distal end portion 328 of the elongate body portion 304. By way of example, the distal end portion 328 may have an enlarged cross-sectional dimension and a rear tapered surface between the distal end portion 328 and the elongate body portion 304. The seal member 326 may include an annular edge having an inwardly extended flange configured to engage the rear tapered surface. Therefore, in some embodiments, the distal end portion 306 of the second plunger 300 may include a combination of the seal member 326 and the distal end 328 of the elongate body portion 304.

Figure 1C:
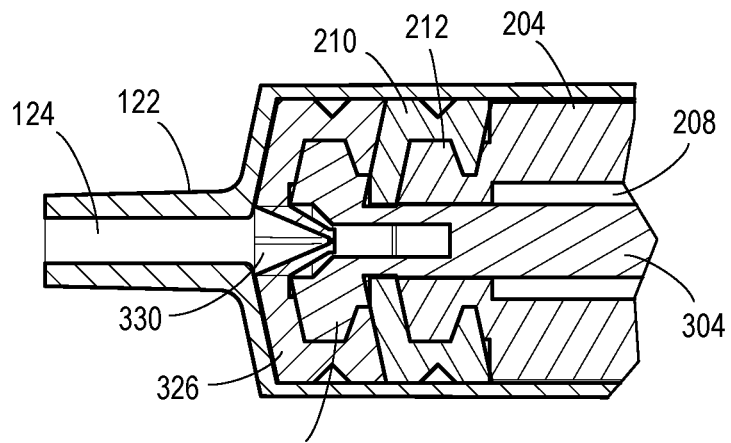
FIG. 1C is a partial enlarged cross-sectional view of the fluid transfer device of FIG. 1B.
Figure 1D:
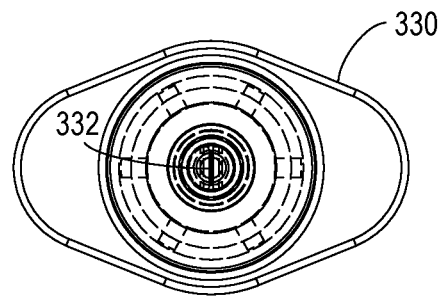
FIG. 1D is an enlarged bottom view of a duckbill check valve incorporated in a fluid transfer device according to some embodiments of the disclosure.

Referring to FIGS. 1B, 1C and 1D, in some embodiments, the distal end portion 306 of the second plunger 300 may include a check valve 330. The check valve 330 may be configured to allow a fluid to pass through in a direction from the distal end portion towards the proximal end portion of the second plunger and prevent a fluid from passing through in a direction from the proximal end portion to the distal end portion of the second plunger. Examples of suitable check valves include but are not limited to duckbill check valves. A duckbill check valve may include an elastomeric lip in the shape of a duckbill. A duckbill check valve may be constructed to allow forward flow with e.g. a positive differential pressure and prevent back flow with a negative differential pressure. The elasticity of the material keeps the bill in the closed position in the absence of a sufficient back pressure. Duckbill check valves are known and commercially available. As shown in greater detail in FIG. 1C, a duckbill check valve 330 may be secured in the seal member 326 with the duckbill portion 332 (FIG. 3) arranged inside the elongate body portion 304 of the second plunger 300. The duckbill check valve 330 may be constructed as a one-piece device and secured in the seal member 326 by a press-fit engagement or other suitable engagement. The duckbill check valve 330 may be aligned with the passageway 124 in the tip 122 of the syringe barrel 110. Other types of check valves can alternatively be used in the second plunger and the present disclosure is not so limited.

Figure 2:
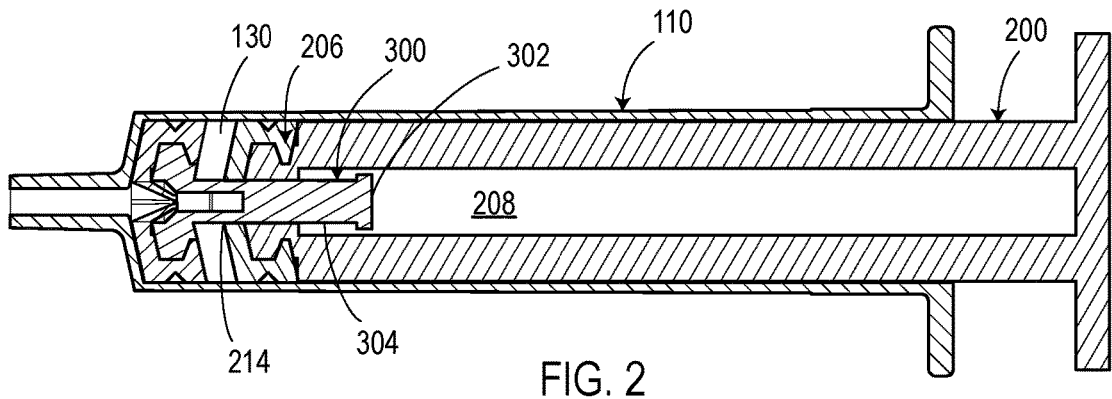
FIG. 2 is a cross-sectional view of a fluid transfer device according to some embodiments of the disclosure, showing the first plunger being retracted to a position.

Referring to FIG. 2, the elongate body portion 304 of the second plunger 300 extends through the opening 214 in the distal end portion 206 of the first plunger 200 and into the internal channel 208 of the elongate body portion 204 of the first plunger 200. The elongate body portion 304 of the second plunger 300 may have a cross-section with an outer dimension smaller than the dimension of the cross-section of the internal channel 208 of the elongate body portion 204 of the first plunger 200 to allow the first plunger 200 to move relative to the second plunger 300. For example, the elongate body portion 304 of the second plunger 300 is slidably movable into and out of the internal channel 208 via the opening 214 when the first plunger 200 moves relative to the second plunger 300. In some embodiments, the elongate body portion 304 of the second plunger 300 is slidably movable in the distal end portion 206 of the first plunger 200, and need not extend into the elongate body portion 204 of wherein the first plunger 200 can slidably move relative to the second plunger 300.

The arrangement of the two plungers allows formation of a sealed volume 130 between the distal end portions of the first and second plungers 200 and 300 for retaining potential dead-leg fluid as will be described in greater detail below. In some embodiments, the elongate body portion 304 of the second plunger 300 may have a substantially smaller cross-section as compared to the cross-section of syringe barrel 110 to allow formation of a bigger sealed volume 130.

A liquid tight seal against the elongate body portion 304 of the second plunger 300 along the circumference of the opening 214 in the distal end portion 206 of the first plunger 200 may be provided. By way of example, the seal member 210 coupled to the distal end portion 212 of the first plunger 200 may be constructed from a resilient and/or pliable material, and the opening 214 may be sized to be slightly smaller than the outer dimension of the cross-section of the elongate body portion 304 of the second plunger 300 to provide a sealing against the elongate body portion 304 when the first plunger 200 is slidably moved relative to the second plunger 300. The seal member 210 coupled to the distal end portion of the first plunger 200 can be made of a material which can provide a low friction sealing surface against the elongate body portion 304 of the second plunger 300. Suitable materials for constructing the seal member 210 include but are not limited to rubbers, silicone, thermoplastic elastomers, and various other materials known in the art.

Figure 3:
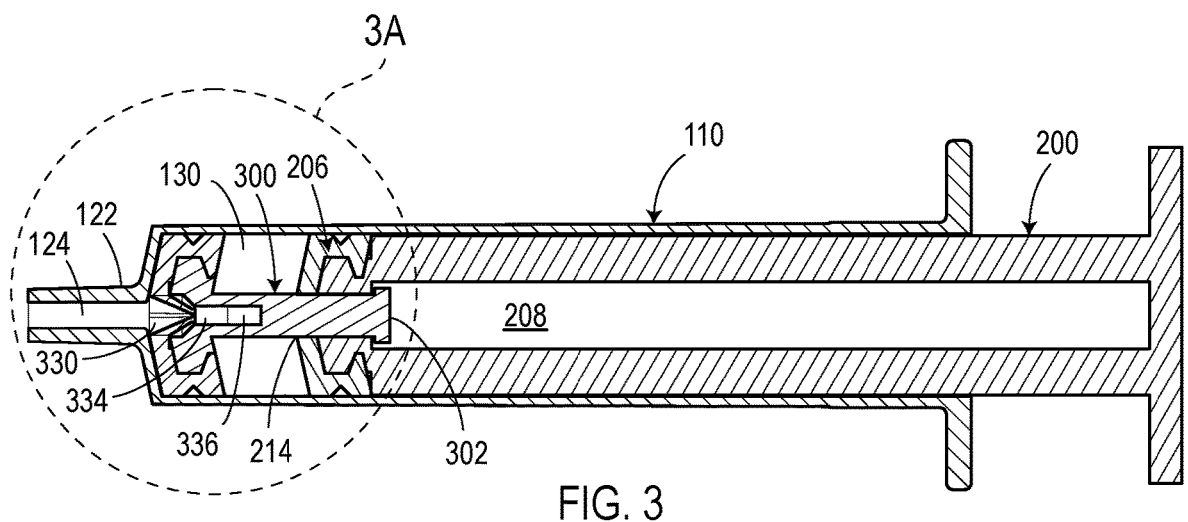
FIG. 3 is a cross-sectional view of a fluid transfer device according to some embodiments of the disclosure, showing the engagement of the first plunger with the second plunger and an isolated volume formed between the first and second plungers.
Figure 3A:
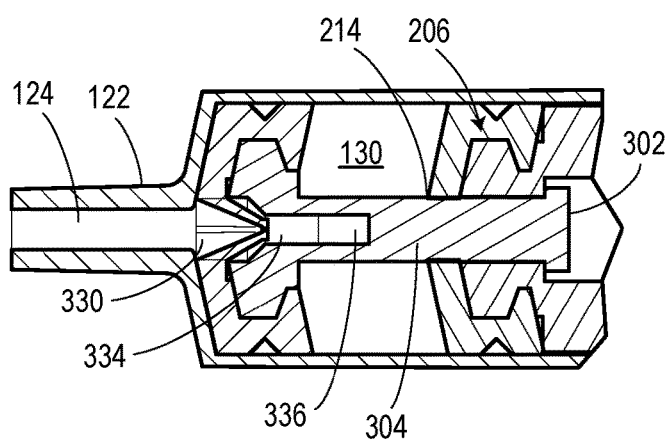
FIG. 3A is a partial enlarged cross-sectional view of the fluid transfer device shown in FIG. 3.

Referring to FIGS. 3 and 3A, the proximal end portion 302 of the second plunger 300 may be configured to engage with the distal end portion 206 of the first plunger 200. By way of example, the proximal end portion 302 of the second plunger 300 may include an outwardly extended flange with a diameter greater than the size of the opening 214 in the distal end portion 206 of the first plunger 200. The proximal end portion 302 may be an integral part of the elongate body portion 304 of the second plunger 300. When the first plunger 200 is retracted to a certain distance, the proximal end portion 302 may be engaged with the distal end portion 206 of the first plunger 200. The engagement allows the second plunger 300 to move with the first plunger 200 when the first plunger 200 is further retracted.

Still referring to FIGS. 3 and 3A, the elongate body portion 304 of the second plunger 300 may have an internal passageway 334 in fluid communication with the check valve 330 and the passageway 124 in the tip 122 of the syringe barrel 110. Openings 336 such as holes, slots or the like may be provided in the elongate body portion 304 of the second plunger 300 such that the internal passageway 334 is also in fluid communication with the sealed volume 130 formed between the distal end portions 206, 306 of the first and second plungers 200, 300.

Returning to FIG. 2, when the proximal end portion 302 of the second plunger 300 and the distal end portion 206 of the first plunger 200 are not engaged, the first plunger 200 is movable relative to the second plunger 300, e.g., the second plunger 300 remains stationary when the first plunger 200 is retracted relative to the syringe barrel 110. This creates a sealed first volume 130 between the distal end portion of the first plunger 200 and the distal end portion of the second plunger 300. The sealed first volume 130 is in its maximum when the proximal end portion of the second plunger 300 and the distal end portion of the first plunger 200 are initially engaged, as shown in FIG. 3. The circumferential seal of the distal end portions of the first and second plungers 200, 300 against the inside surface of the syringe barrel 110 creates a vacuum or negative pressure in the sealed first volume 130. This allows flow of a fluid into the sealed first volume 130 via the passageway 124 in the tip 122 of the syringe barrel 110, the check valve 330, the internal passageway 334 and openings 336 in the elongate body portion 304 of the second plunger 300.

Figure 4:
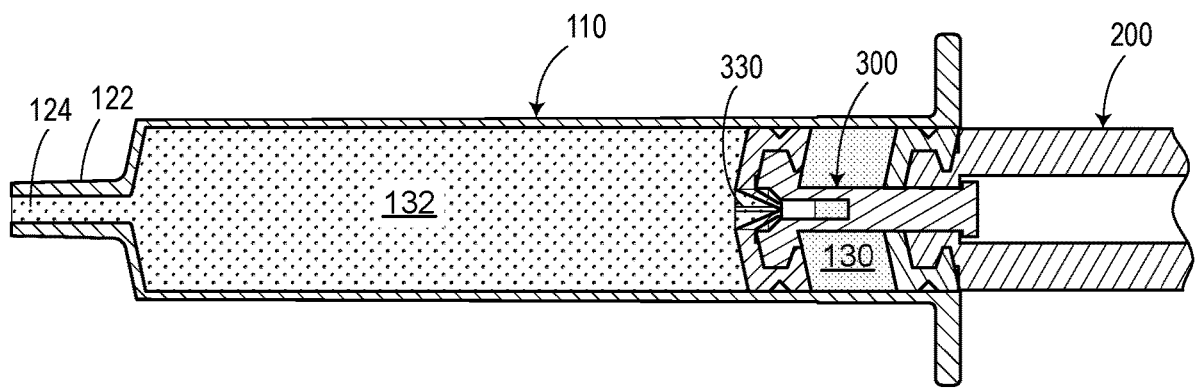
FIG. 4 is a cross-sectional view of a fluid transfer device according to some embodiments of the disclosure, illustrating drawing of a representative sample into the syringe barrel by retracting the first plunger engaged with the second plunger.

Referring to FIG. 4, when the proximal end portion of the second plunger 300 and the distal end portion of the first plunger 200 are engaged, further retraction of the first plunger 200 allows the second plunger 300 to move with the first plunger 200. The movement of the second plunger 300 with the first plunger 200 creates a second volume 132 between the distal end portion of the second plunger 300 and the distal end portion of the syringe barrel 110. The circumferential seal of the distal end portion of the second plunger 300 against the syringe barrel 110 creates a vacuum or negative pressure in the second volume 132. This allows a representative sample to be drawn into the second volume 132 via the passageway 124 in the tip 122 of the syringe barrel 110.

The incorporation of the check valve 330 in the second plunger 300 prevents the fluid e.g. dead-leg fluid in the first volume 130 from flowing back into the second volume 132 which retains the representative sample. The use of the check valve 330 allows the fluid in a dead-leg or trap of tubing and/or valves of the fluid transfer system to be cleared and isolated in the sealed first volume 130 before a representative sample is drawn. Fluid in a dead-leg or trap of the tubing and sampling valves may have stagnated over a long period of time and would result in an inaccurate reading of a representative sample if contaminated or mixed with the dead-leg fluid. Conventionally, a separate standard syringe is used to clear the tubing and valves by drawing a full sample. The syringe with the full sample is disconnected and discarded. Then a new syringe is connected to take a representative sample.

According to certain embodiments of this disclosure, the fluid transfer device 100 described above can be used to both clear and isolate potential dead-leg fluid and take a representative sample. Fluid in dead-legs of tubing and valves may be drawn into the sealed first volume 130. The check valve 330 prevents back flow of the dead-leg fluid and thus keeps the dead-leg fluid isolated in the sealed first volume 130. A representative sample is then drawn, via the tubing and valves which have been cleared. The representative sample may be retained in the second volume 132.

The volume of potential dead-leg fluid can be pre-determined based on the tubing and valves used in a fluid transfer system. The maximal capacity of the sealed first volume 130 can be defined to accommodate at least all of the dead-leg fluid. By way of example, the length of the elongate body portion of the second plunger 300 and the dimension of the cross-section of the syringe barrel 110 may be configured to provide a maximal capacity of the first volume 130 for retaining a fluid ranging from about 1 ml to about 50 ml.

Figure 5:
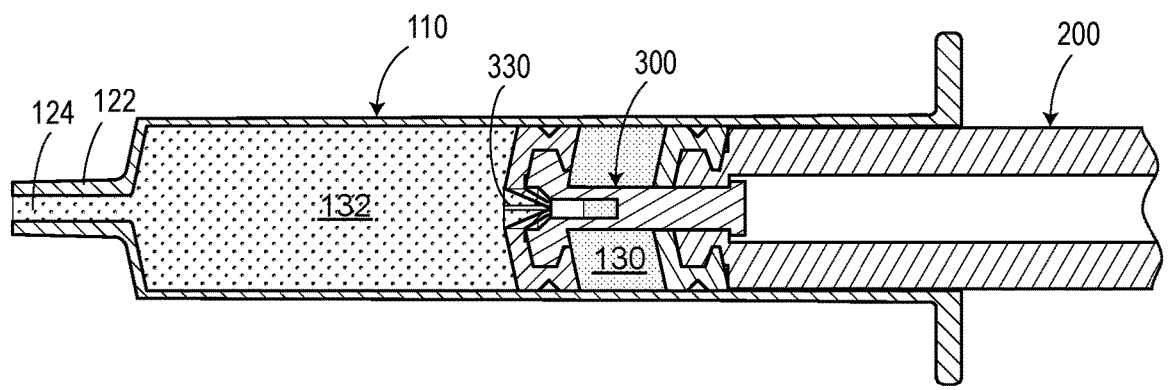
FIG. 5 is a cross-sectional view of a fluid transfer device according to some embodiments of the disclosure, illustrating dispensing of the representative sample by pushing the first plunger engaged with the second plunger.

Referring to FIG. 5, the representative sample may be subsequently dispensed for analysis by pushing the first plunger 200. The check valve 330 built into the distal end portion of the second plunger 300 retains the dead-leg fluid within the sealed first volume 130 when the first plunger 200 is pushed. Pushing the first plunger 200 applies a pressure to the second volume, allowing the representative sample to be dispensed from the second volume 132.

Figure 6:
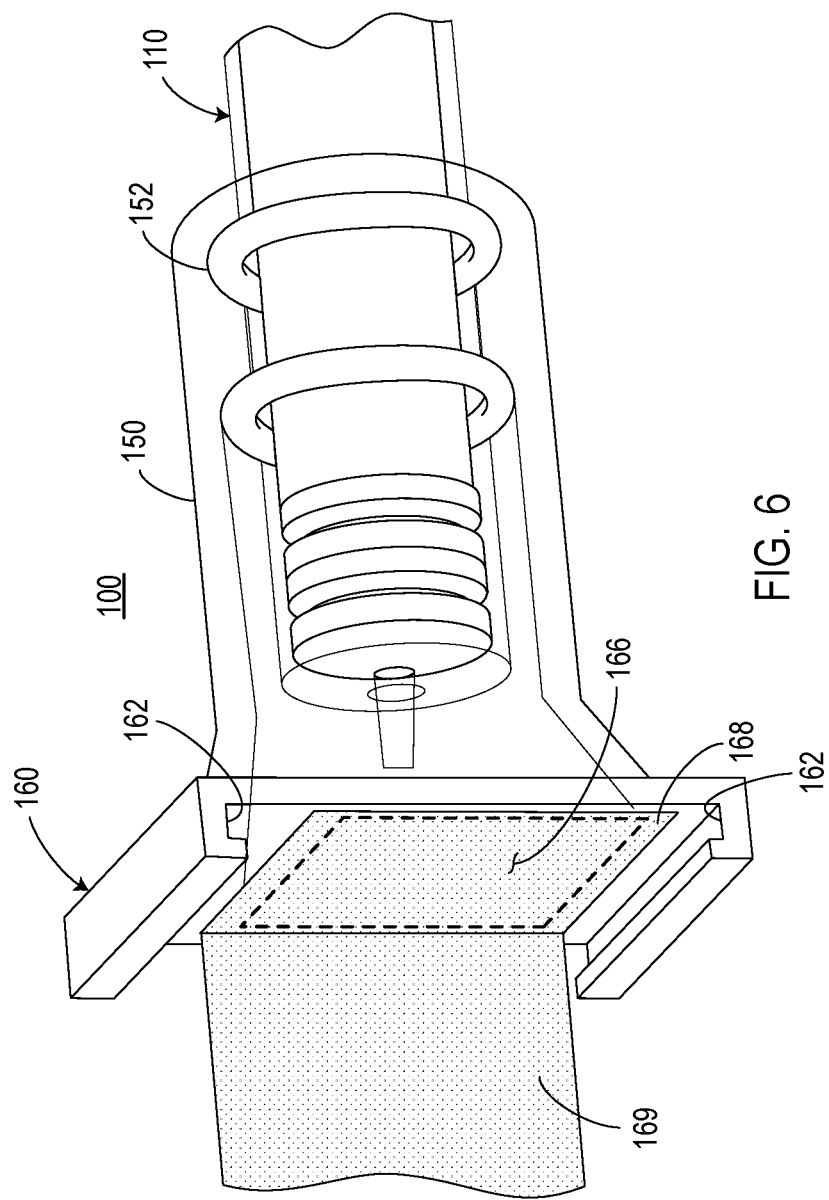
FIG. 6 schematically shows a fluid transfer device including a housing enclosing a distal end portion of the device according to some embodiments of the disclosure.

Referring to FIG. 6, in some embodiments, the fluid transfer device 100 may further include a housing 150. The housing 150 may function to protect the fluid transfer device from contamination and/or facilitate coupling of the fluid transfer device with a sampling device. For example, the housing 150 may be constructed or configured to shroud or enclose a distal end portion of the device 100, including any tip portion of the syringe barrel configured to engage with a sampling device. The housing 150 can be configured to allow the syringe barrel 110 to axially slide into and out of the inside of the housing 150 for engaging with or disengaging from a sampling device. One or more seals such as O-rings or the like 152 may be provided to seal the distal end portion of the device 100 from the ambient environment.

The fluid transfer device 100 may include an interface structure 160 configured to couple with a complementary interface structure in a sampling device as will be described in greater detail below. The interface structure 160 may include any suitable mating structure configured to engage with a complementary mating structure in a sampling device. As shown in FIG. 6, the exemplary interface structure 160 includes one or more grooves 162 configured to slidably engage with one or more tongues in a sampling device. The interface structure 160 shown in FIG. 6 includes a frame-like member having an opening 166 covered by a protective film 168. A pair of parallel grooves 162 are provided on opposite sides of the frame-like member configured to slidably engage with a pair of tongues in the complementary interface structure of a sampling valve.

The protective film 168 is configured to cover the opening 166 of the housing 150 to protect the device 100, including the tip to be engaged with a sampling device, from contamination by dust, dirt, bacteria or the like. The protective film 168 may be in the form of paper, metal foils, polymeric films or the like. The protective film 168 may be attached to the interface structure 160 via bonding or other suitable means, and can be peeled off or otherwise removed from the interface structure 160. The protective film 168 may include an extra length 169, tab or the like for ease of peeling off the film from the interface structure 160 after the interface structure 160 of the fluid transfer device 100 is coupled with a complementary interface structure in a sampling device or during the coupling of the fluid transfer device 100 with a sampling device as will be described in greater detail below.

Referring to FIGS. 7-12, various embodiments of a fluid transfer assembly 400 according to another aspect of the disclosure will now be described.

Figure 7:
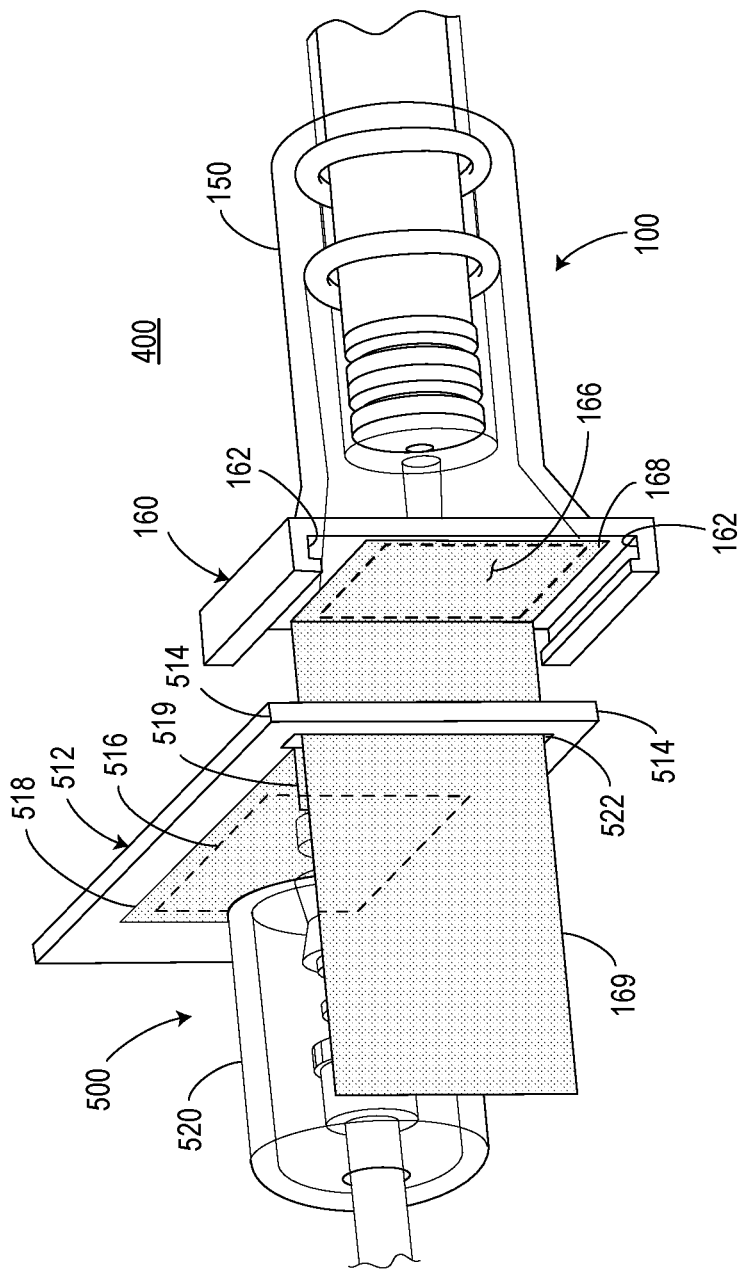
FIG. 7 schematically shows a fluid transfer assembly according to some embodiments of the disclosure, including a first transfer device, a second fluid transfer device, and interface structures on each of the first and second fluid transfer devices.

As shown in FIG. 7, the fluid transfer assembly 400 includes a first fluid transfer device 500 and a second fluid transfer device 100. The first fluid transfer device 500 may include an interface structure 512. The second fluid transfer device 100 may include an interface structure 160 complementary to the interface structure 512 of the first fluid transfer device 500. The first and second interface structures 512 and 160 may be configured to slidably engage one another, allowing the second fluid device 100 to slidably move to position or align with the first fluid transfer device 500. The first fluid transfer device 500 may be configured to connect to a fluid source such as a reactor or container or a conduit in fluid communication with a reactor or container. The second fluid transfer device 100 may be configured to aseptically engage with the first fluid transfer device 500 for sampling the fluid source via the first fluid transfer device 500.

The interface structure 512 of the first fluid transfer device 500 may include a mating structure such as one or more tongues 514. The interface structure 160 of the second fluid transfer device 100 may include a mating structure such as one or more grooves 162 to allow the interface structures 512 and 160 slidably engage one another. Alternatively, the interface structure of the first fluid transfer device 500 includes one or more grooves and the interface structure of the second fluid transfer device 100 includes one or more complementary tongues. A locking mechanism such as latches, slots, forks, stops or the like (not shown) may be included in the interface structures to secure the coupling once the devices are put in place.

Still referring to FIG. 7, in some embodiments, the first fluid transfer device 500 may include a housing 520, and the interface structure 512 may be a part of the housing 520. The second fluid transfer device 100 may include a housing 150 and the interface structure 160 may a part of the housing 150. As such, the interface structure 512 may include a frame-like member having an opening 516 covered by a protective film 518 to protect the device 500 enclosed inside the housing 520 from contamination. The interface structure 160 may include a frame-like member having an opening 166 covered by a protective film 168 to protect the device 100 or a distal end portion of the device 100 enclosed inside the housing 150 from contamination. Once the first and second fluid transfer devices 500 and 100 are positioned in place or properly aligned relative to one another, the protective films 518 and 168 can be removed, opening up the housings 520 and 150 or creating a pass-through for coupling or engagement of the second fluid transfer device 100 with the first fluid transfer device 500. The interface structures 512 and 160 may be constructed such that when the second fluid transfer device 100 is positioned in place with the first fluid transfer device 500 and the protective films 168 and 518 are removed, the interface structures 512, 160 abut one another, forming a seal for the housings 520 and 150 from the ambient environment.

The interface structure 512 of the first fluid transfer device 500 may be a separately constructed unit assembled to the housing 520, or alternatively, is integral with the housing 520. The interface structure 160 of the second fluid transfer device 100 may be a separately constructed unit assembled to the housing 150, or alternatively, is integral with the housing 150. The housings 520 and 150 of the first and second fluid transfer devices 500 and 100 can be constructed with any suitable material such as plastic, metal or the like. The housings 520 and 150 can be transparent, semi-transparent or non-transparent.

Still referring to FIG. 7, the protective films 518 and 168 may be attached to the interface structures 512 and 160 respectively via bonding or other suitable means, and are both removable e.g. by peeling or pulling. The protective films 518 and 168 can be constructed from a suitable material that precludes passage of contaminants such as dust, dirt, bacteria or the like, and can be in the form of paper, metal foils, polymeric films or the like. In some embodiments, the protective films 518 and 168 may each have an extended portion 519 and 169 that sinks or passes through a slot 522 in the interface structure 512 of the first fluid transfer device 500 for ease of peeling off the films 518 and 168 attached to the interface structures 512 and 160 after the second and first fluid transfer devices 100 and 500 are positioned in place as will be described in greater detail below.

The initial assembling of the first and second fluid transfer devices 500 and 100 may be accomplished by slidably joining them via their interface structures 512 and 160. For example, in an embodiment where the interface structure of the first fluid transfer device 500 includes tongues or grooves and the interface structure of the second fluid transfer device 100 includes complementary grooves or tongues, the tongues and grooves in the corresponding interface structures may be aligned and joined by sliding the second fluid transfer device 100 against the first fluid transfer device 500. The extended portion 169 of the protective film 168 of the second fluid transfer device 100 may sink through the slot 522 in the first fluid transfer device 500 before the tongues and grooves are aligned and joined. During the sliding of the second fluid transfer device 100 relative to the first fluid transfer device 500, the extended film portion 169 may be pulled back through the slot 522 and folded over the second fluid transfer device 100. Thus, the length of the extended film portion 169 may be selected such that its end portion remains outside of the slot 522 once the second fluid transfer device 100 is slidably positioned or aligned with the first fluid transfer device 500, to allow pulling of the film 168 attached to the interface structure 160.

Figure 8:
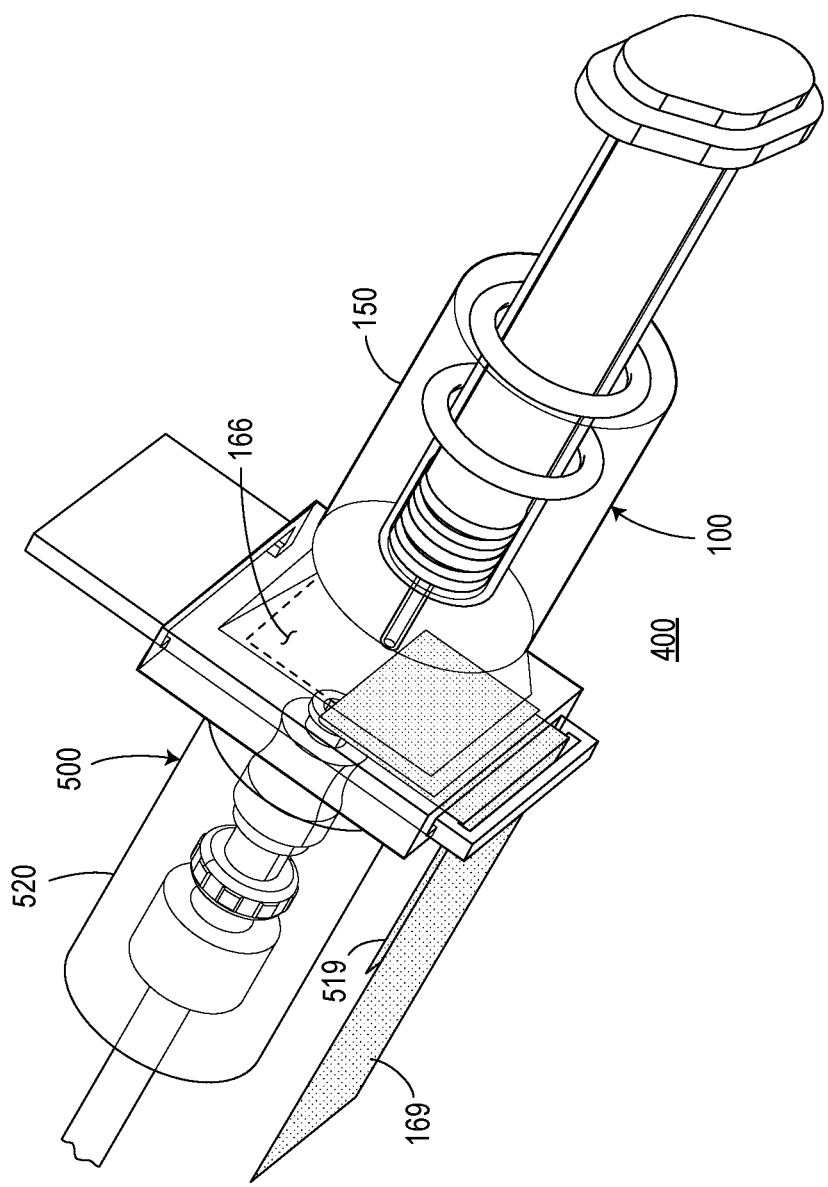
FIG. 8 schematically shows positioning of the second fluid transfer device in place with the first fluid transfer device and removing the protective films on the interface structures on each of the first and second fluid transfer devices.
Figure 9:
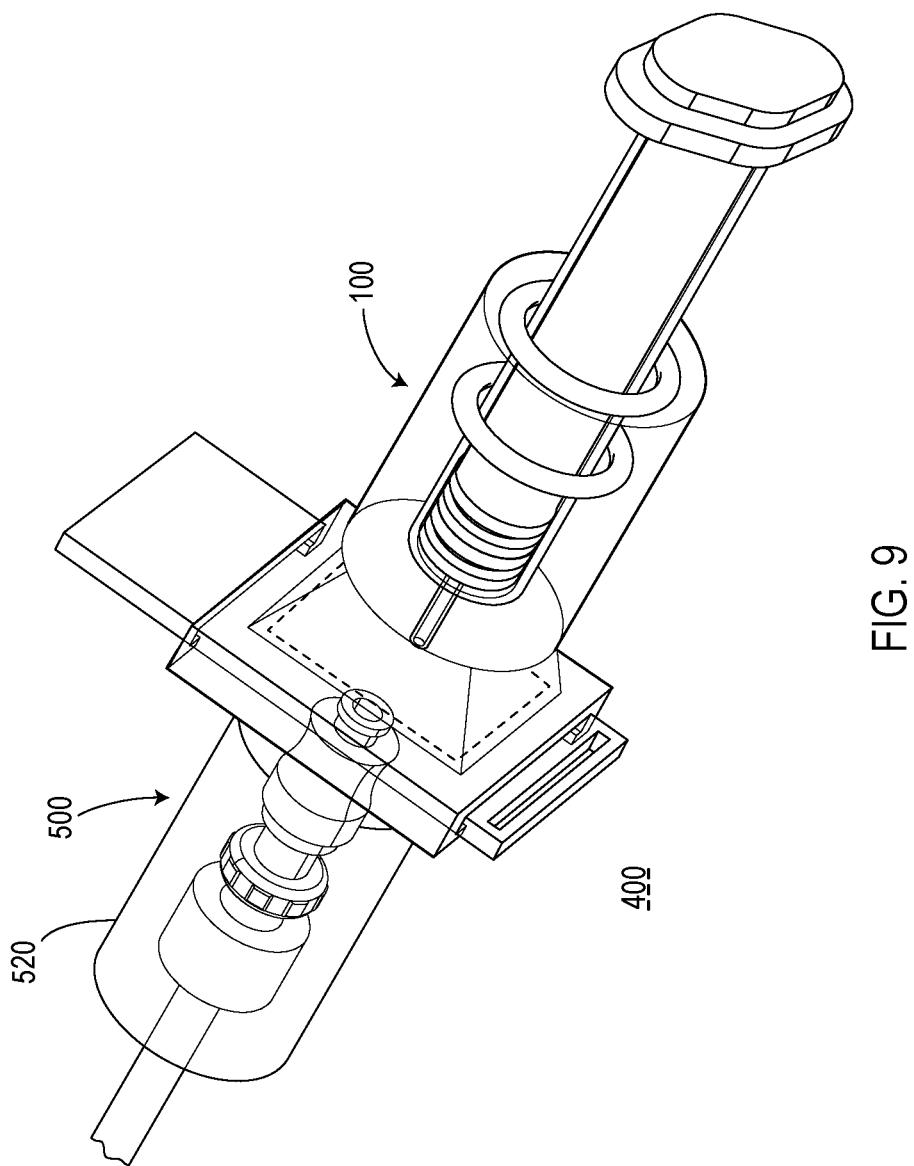
FIG. 9 schematically shows positioning of the second fluid transfer device in place with the first fluid transfer device with the protective films being removed.

Once the second fluid transfer device 100 is positioned in place or aligned with the first fluid transfer device 500, the protective films 518 and 168 attached to the first and second interface structures 512 and 160 can be removed e.g. by pulling or peeling, thereby opening up the housings 520 and 150 respectively and creating a pass-through for coupling or engagement of the second fluid transfer device 100 with the first fluid transfer device 500. FIG. 8 shows that the second fluid transfer device is positioned in place with the first fluid transfer device 500 and the protective films 518 and 168 are being peeled off. FIG. 9 shows that the protective films 518 and 168 are completely removed, creating a pass-through to allow engagement of the second fluid transfer device 100 with the first fluid transfer device 500.

The second fluid transfer device 100 may engage with the first fluid transfer device 500 by e.g. axially pushing the second fluid device 100 against the first fluid device 500. Sample fluid can then be drawn by the second fluid transfer device 100 via the first fluid transfer device 500.

In some embodiments, the second fluid transfer device 100 may include a syringe barrel, two plungers and a check valve as described above in conjunction with FIGS. 1-5. As such, fluid in the dead-legs, e.g., of the tubing connecting to the fluid source and/or in the valve of the first fluid device 500 may be cleared by drawing it into a sealed first volume in the second fluid transfer device 100. The incorporation of the check valve prevents back flow of the dead-leg fluid and keeps it isolated in the first volume. A representative sample can then be drawn into the second volume which is isolated from the first volume by the check valve.

After a representative sample is drawn, the second fluid transfer device 100 may be disengaged from the first fluid transfer device 500, then displaced or removed e.g., to allow the sample to be dispensed for analysis, and/or to allow a next or a third fluid transfer device to position and engage with the first fluid transfer device 500 for taking additional sample from the fluid source. The second fluid transfer device 100 may be disengaged from the first fluid transfer device 500 by e.g. axially retracting the second fluid device 100 away from the first fluid device 500. The second fluid transfer device 100 can then be displaced from the position of the first fluid transfer device 500 by sliding via the interface structures 512 and 160.

Figure 10:
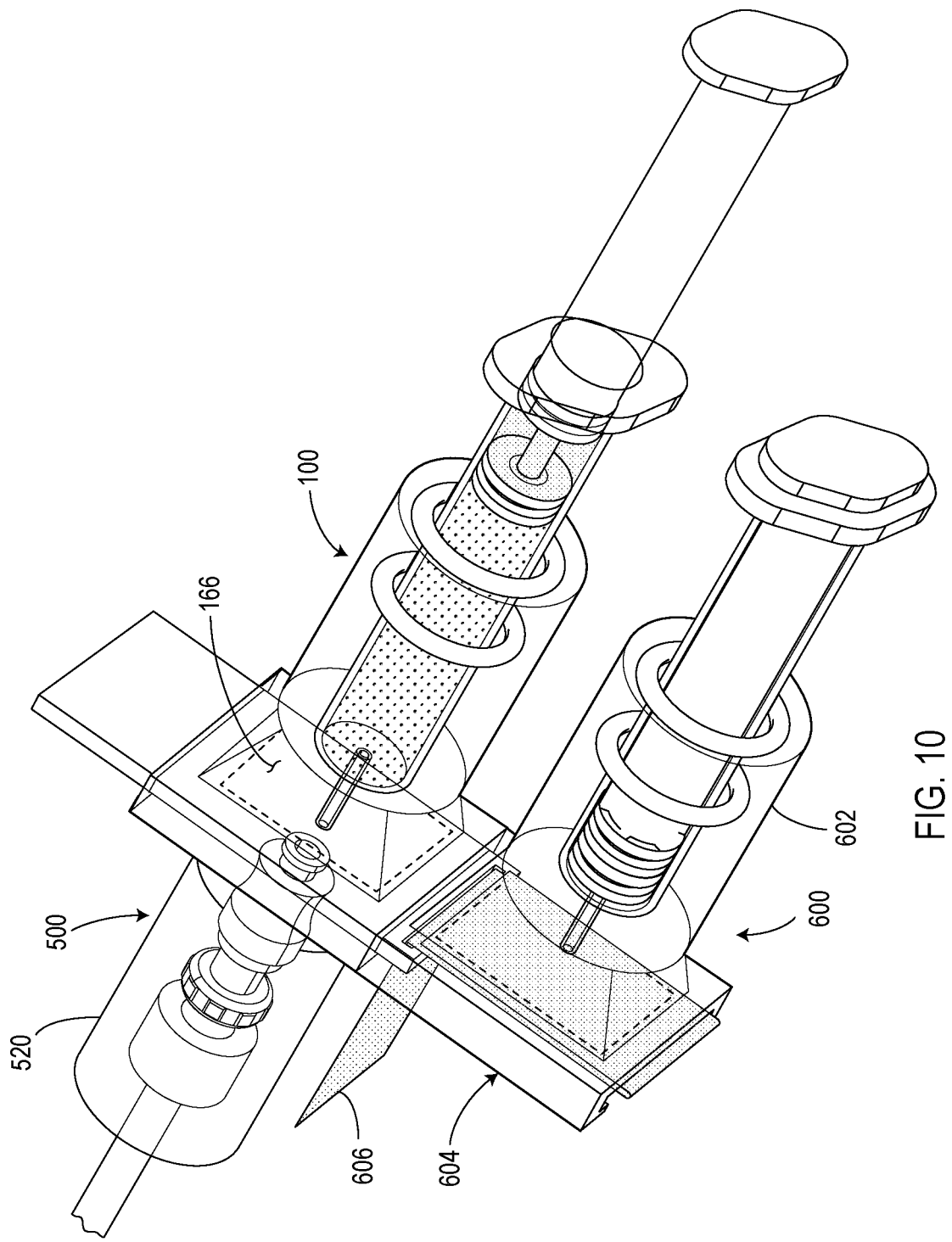
FIG. 10 schematically shows replacement of the second fluid transfer device with a next third fluid transfer device according to some embodiments of the disclosure.

FIG. 10 illustrates a method of replacing the second fluid transfer device 100 with a third fluid transfer device 600. The third fluid transfer device 600 may have a structure identical or substantially identical with the second fluid transfer device 100. Alternatively, the third fluid transfer device 600 may have a structure different from the second fluid transfer device 100. The third fluid device 600 may include a housing 602 enclosing a distal end portion of the device, an interface structure 604 such as one or more grooves, and a protective film 606 removably attached to the interface structure 604 covering an opening in the housing 602. The protective film 606 may have an extra length or tab that can pass through the slot 522 in the interface structure of the first fluid transfer device 500.

Referring to FIG. 10, in some embodiments, the displacing of the second fluid transfer device 100 from the first fluid transfer device 500 and the positioning of the third fluid transfer device 600 with the first fluid transfer device 500 may be carried out at the same time. This can be accomplished by slidably pushing the third fluid transfer device 600 against the second fluid transfer device 100 via the interface structures such that the third fluid transfer device 600 is placed in position with the first fluid transfer device 500 at the time when the second fluid transfer device 100 is displaced from the first fluid transfer device 500. The protective film 606 attached to the third fluid transfer device 600 can be peeled gradually while the third fluid transfer device 600 is pushed against the second fluid transfer device 100, thereby gradually opening up the housing 602 of the third fluid transfer device 600 and aseptically connecting housing 602 with the housing 520 of the first fluid device 500. In other words, the protective film 606 over the third fluid transfer device 600 may be removed in sync with the positioning of the third fluid transfer device 600 with the first fluid transfer device 500. The protective film 606 can be completely removed once the third fluid transfer device 600 is positioned in place or aligned with the first fluid transfer device 500. The replacement method according to the embodiment described above is beneficial because the sterility of the system can be preserved while the earlier or second fluid transfer device 100 is being replaced with the next or third fluid transfer device 600.

Figure 11:
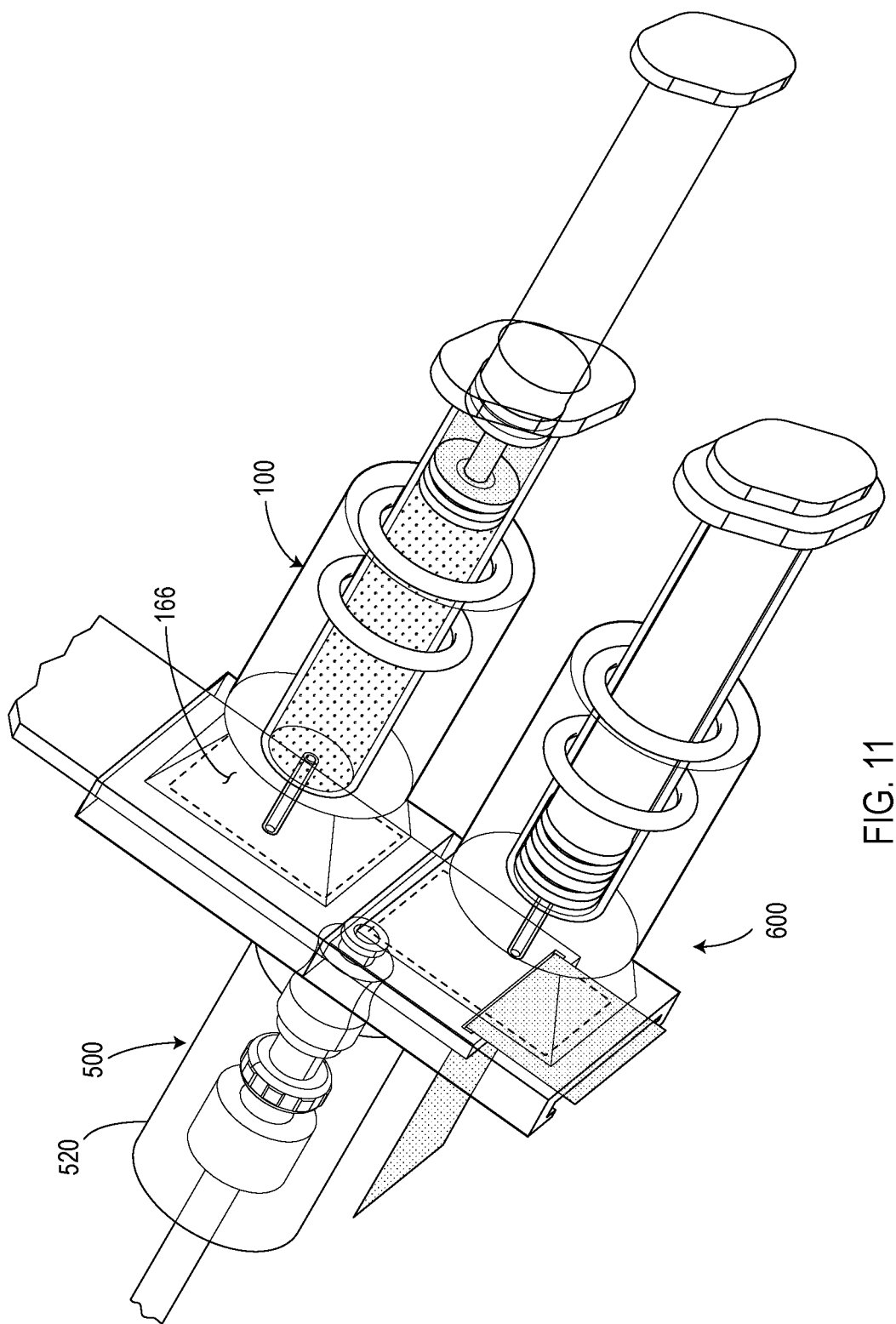
FIG. 11 schematically shows the replacement-in-progress of the second fluid transfer device with the third fluid transfer device according to some embodiments of the disclosure.
Figure 12:
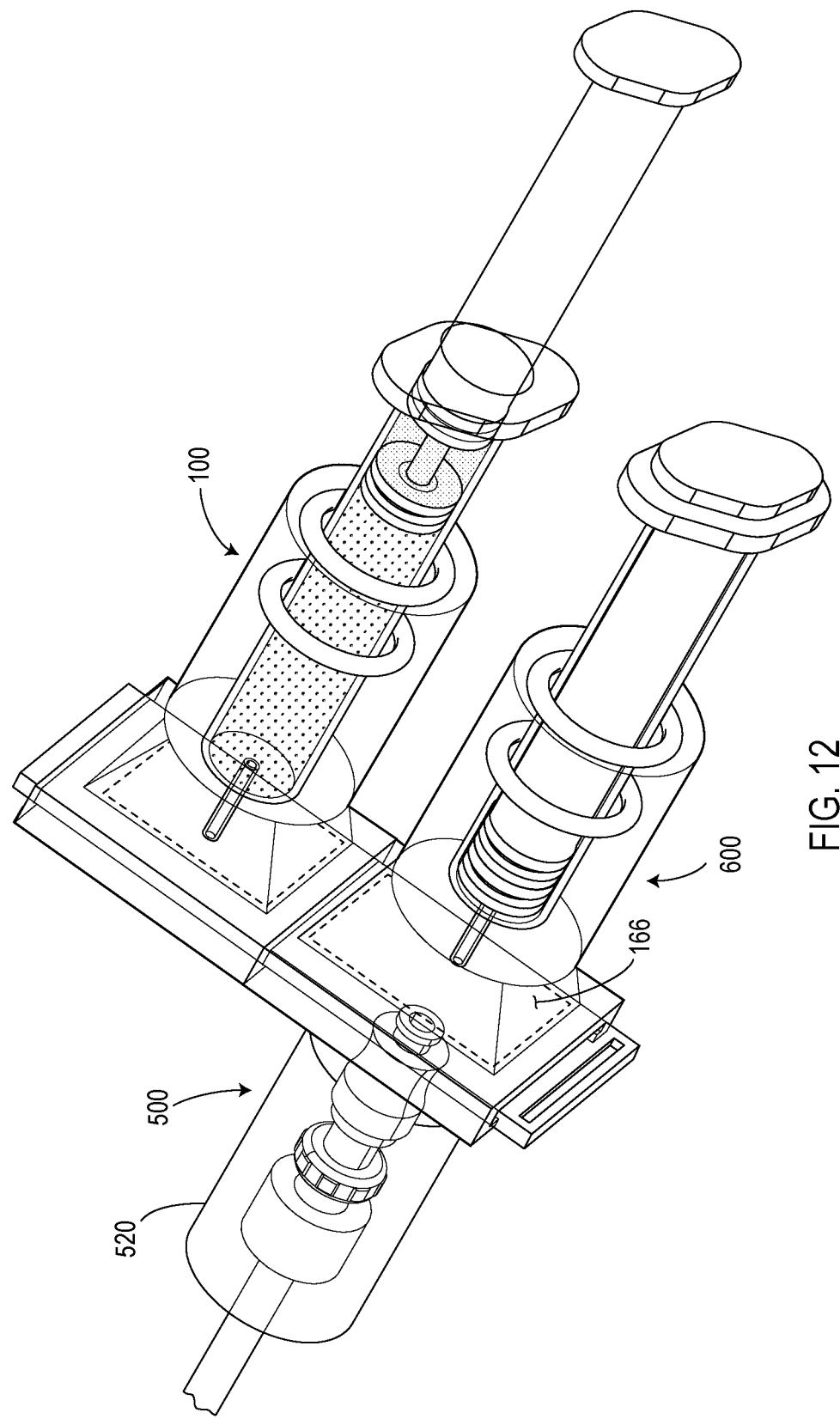
FIG. 12 schematically shows the completion of the replacement of the second fluid transfer device with the third fluid transfer device according to some embodiments of the disclosure.

FIG. 11 schematically shows the replacement in progress when the earlier or second fluid transfer device 100 is being displaced from the position with the first fluid transfer device 500, the third fluid transfer device 600 is being positioned in place with the first fluid transfer device 500, and the protective film 606 is being peeled while the third fluid transfer device 600 is sliding against the first fluid transfer device 100, gradually opening up and aseptically connecting the housing of the third fluid transfer device 600 with the housing of the first fluid transfer device 500. FIG. 12 schematically shows that the second fluid transfer device 100 is displaced from the first fluid transfer device 500, the third fluid transfer device 600 is positioned or aligned with the first fluid transfer device 500, and the protective film over the third fluid transfer device 600 is completely removed.

Once the third fluid transfer device 600 is positioned in place, and coupled or engaged with the first fluid transfer device 500, an additional representative sample may be drawn in the manner same or similar to that described above in connection with the second fluid transfer device 100.

The first fluid transfer device 500 can be any suitable sampling device including such as a luer activated valve sampling device. Various luer activated valves are known in the art and their detailed description is omitted herein in order to focus the description of embodiments of this disclosure. U.S. Pat. No. 8,544,497 to the present assignee discloses various embodiments of valves that can be used as the first fluid transfer device of this disclosure. The disclosure of U.S. Pat. No. 8,544,497 is incorporated herein by reference in its entirety.

The second fluid transfer device 100, the third fluid transfer device 600, or any subsequent fluid transfer devices to be coupled with the first fluid transfer device 500 may comprise any suitable syringe devices available in the art. In some preferred embodiments of the disclosure, the second, third, and subsequent fluid transfer devices may include a syringe barrel, two plungers each slidably movable inside the syringe barrel, and a check valve as described above in conjunction with FIGS. 1-5.

The terms "first," "second," and "third" are used herein for ease of description of various embodiments and it should be understood that a "third" can become a "second" after a "third" fluid transfer device replaces a "second" fluid transfer device and that the term "third" includes reference to a plurality of fluid transfer devices having an identical or substantially identical structure.

A fluid transfer device, assembly, and method have been described. Those skilled in the art will appreciate that various other modifications may be made within the spirit and scope of the invention. All these or other variations and modifications are contemplated by the inventors and within the scope of the invention.

What is claimed is:

1. A fluid transfer device, comprising: a syringe barrel having an inside surface defining a chamber and a distal end portion comprising a passageway; a first plunger slidably movable inside the chamber, the first plunger comprising a proximal end portion, an elongate body portion, and a distal end portion, the distal end portion of the first plunger providing a circumferential seal against the inside surface of the syringe barrel; and a second plunger slidably movable inside the chamber, the second plunger comprising a proximal end portion, an elongate body portion, and a distal end portion, the distal end portion of the second plunger providing a circumferential seal against the inside surface of the syringe barrel, wherein the distal end portion of the first plunger is engageable with the proximal end portion of the second plunger such that when the distal end portion of the first plunger and the proximal end portion of the second plunger are engaged, the second plunger is movable by the first plunger, wherein the elongate body portion of the first plunger comprises an internal channel and the distal end portion of the first plunger has a pass-through into the internal channel; and the elongate body portion of the second plunger is slidably movable through the pass-through, and the proximal end portion of the second plunger is engageable with the distal end portion of the first plunger, wherein the pass-through in the distal end portion of the first plunger provides a circumferential seal against the elongate body portion of the second plunger.

2. The fluid transfer device of claim 1, wherein a sealed first volume is defined between the distal end portion of the first plunger and the distal end portion of the second plunger when the first plunger is proximally moved relative to the second plunger, and a second volume is defined between the distal end portion of the second plunger and the distal end portion of the syringe barrel when the second plunger is proximally moved by the first plunger.

3. The fluid transfer device of claim 2, wherein the elongate body portion of the second plunger has an internal passageway in fluid communication with the sealed first volume.

4. The fluid transfer device of claim 3, wherein the second plunger further comprises a check valve in the distal end portion.

5. The fluid transfer device of claim 4, wherein the distal portion of the second plunger comprises a seal member and the check valve is integrated in the seal member.

6. The fluid transfer device of claim 1, further comprising a housing enclosing the fluid transfer device or distal portion thereof, wherein the housing has an opening covered by a protective film and comprises an interface structure.

7. The fluid transfer device of claim 6 wherein the interface structure comprises one or more grooves that are complementary with one or more tongues on a sampling device, or wherein the interface structure comprises one or more tongues that are complementary with one or more grooves on a sampling device.

8. The fluid transfer device of claim 6, wherein the protective film is removably attached to the interface structure.

* * * * *